United States Patent
Forman

(10) Patent No.: US 12,404,502 B2
(45) Date of Patent: *Sep. 2, 2025

(54) HYBRID YEAST CELL LINES FOR HIGH LEVEL PRODUCTION OF RECOMBINANT PROTEIN

(71) Applicant: CHO Plus, Inc., San Mateo, CA (US)

(72) Inventor: Lawrence Forman, San Mateo, CA (US)

(73) Assignee: CHO Plus, Inc.

( * ) Notice: Subject to any disclaimer, the term of this patent is extended or adjusted under 35 U.S.C. 154(b) by 247 days.

This patent is subject to a terminal disclaimer.

(21) Appl. No.: 17/721,930

(22) Filed: Apr. 15, 2022

(65) Prior Publication Data

US 2022/0243192 A1 Aug. 4, 2022

Related U.S. Application Data

(63) Continuation of application No. 16/440,776, filed on Jun. 13, 2019, now Pat. No. 11,649,449, which is a continuation of application No. PCT/US2019/036379, filed on Jun. 10, 2019, and a continuation-in-part of application No. 15/254,852, filed on Sep. 1, 2016, now Pat. No. 10,329,594.

(60) Provisional application No. 62/213,880, filed on Sep. 3, 2015.

(51) Int. Cl.
| | | |
|---|---|---|
| *C12N 15/02* | (2006.01) | |
| *C12N 5/071* | (2010.01) | |
| *C12N 5/16* | (2006.01) | |
| *C12N 15/10* | (2006.01) | |

(52) U.S. Cl.
CPC .......... *C12N 15/02* (2013.01); *C12N 5/0682* (2013.01); *C12N 5/16* (2013.01); *C12N 15/10* (2013.01)

(58) Field of Classification Search
CPC .............. G01N 33/56966; C12N 15/02; C12N 5/0682; C12N 5/16; C12N 15/10
See application file for complete search history.

(56) References Cited

U.S. PATENT DOCUMENTS

| | | | |
|---|---|---|---|
| 5,607,845 | A | 3/1997 | Spira et al. |
| 6,136,599 | A | 10/2000 | Cho |
| 6,420,140 | B1 | 7/2002 | Hori et al. |
| 7,429,380 | B2 | 9/2008 | Hori et al. |
| 9,816,110 | B2 | 11/2017 | Shen et al. |
| 10,329,594 | B1 * | 6/2019 | Forman ................. C12N 5/12 |
| 11,013,250 | B2 | 5/2021 | Vrijic et al. |
| 11,649,449 | B2 * | 5/2023 | Forman ................. C12N 15/10 435/68.1 |
| 2004/0077090 | A1 | 4/2004 | Short |
| 2008/0145861 | A1 | 6/2008 | Rapp et al. |
| 2012/0015841 | A1 * | 1/2012 | Shekdar ................. A61P 3/10 435/6.12 |
| 2015/0305390 | A1 | 10/2015 | Vrljic et al. |
| 2019/0322999 | A1 | 10/2019 | Forman |
| 2022/0243192 | A1 | 8/2022 | Forman |
| 2022/0243193 | A1 | 8/2022 | Forman |
| 2024/0167006 | A1 | 5/2024 | Form et al. |

FOREIGN PATENT DOCUMENTS

| | | |
|---|---|---|
| CN | 1339063 A | 3/2002 |
| KR | 20120058497 A | 6/2012 |
| WO | 0104306 A1 | 1/2001 |
| WO | 2006027202 A1 | 3/2006 |
| WO | 2009103753 A1 | 8/2009 |
| WO | 2018232265 A1 | 12/2018 |
| WO | 2019010551 A1 | 1/2019 |

OTHER PUBLICATIONS

Tartakoff. Cell Biology of Yeast Zygotes, from Genesis to Budding. Biochim. Biophys. Acta 1853 (7): 1702-1714 (Jul. 2015).*
"CHO-K1", ATCC.Com, Available online at: https://www.atcc.org/products/ccl-61?matchtype=&network=g&%20device=c&adposition=&keyword=&gad_source=1&gclid=%20EAlaIQobChM%20lteGOooS-hwMVBDM%20IBR1E8AHAEAAYASAAEgJ%20MdvD_BwE%3E, 2024, 6 pages.
"Drug Approval Process", Food and Drug Administration, 2022, 2 pages.
Chakrabarti et al., "Mitochondrial Membrane Potential Identifies Cells With High Recombinant Protein Productivity", Journal of Immunological Methods, vol. 464, Jan. 2019, pp. 31-39.
Davies , "Cell Sorting by Flow Cytometry", Available online at: https://link.springer.com/chapter/10.1007/978-1-59745-451-3_11#preview, 2007, pp. 257-276.
Dorner et al., "The Levels of Endoplasmic Reticulum Proteins and ATP Affect Folding and Secretion of Selective Proteins", Biologicals, vol. 22, No. 2, Jun. 1994, pp. 103-112.
Dumont et al., "Human Cell Lines for Biopharmaceutical Manufacturing: History, Status, and Future Perspectives", Critical Reviews in Biotechnology, vol. 36, No. 6, Dec. 2016, pp. 1110-1122.
Application No. EP19933147.1 , Extended European Search Report, Mailed on Dec. 13, 2022, 8 pages.
Hernandez et al., "The Hallmarks of Cell-Cell Fusion", The Company of Biologists Limited, vol. 144, No. 24, Dec. 15, 2017, pp. 4481-4495.

(Continued)

*Primary Examiner* — Gailene Gabel
(74) *Attorney, Agent, or Firm* — Michael Schiff

(57) ABSTRACT

This disclosure provides improved cell lines for manufacture of protein, considerably reducing the cost of commercial production. The cell lines are obtained by selecting cells from a mixed population for one or more characteristics that support protein production on a non-specific basis, such as the level of endoplasmic reticulum, Golgi apparatus, and/or other desired phenotypic features, compared with other cells in the starting mixture. Particularly effective producer cell lines can be obtained by preparing the cells for functional selection by making cell hybrids. A gene encoding a heterologous protein of interest may be transfected into the cells before or after one or more cycles of fusion and selection. Depending on the protein product being expressed, cell lines may be obtained that produce eight grams or more of protein per liter of culture fluid.

10 Claims, 1 Drawing Sheet

(56) References Cited

OTHER PUBLICATIONS

Huang et al., "Maximizing Productivity of Cho Cell-based Fed-batch Culture Using Chemically Defined Media Conditions and Typical Manufacturing Equipment", vol. 26, No. 5, 2010, pp. 1400-1410.

Lai et al., "Increased Antibody Productivity in Chinese Hamster Ovary Cells Through Induction of Chromosomal Instability by Cell Fusion", Poster at ESACT Meeting 2015 in Barcelona, May 31-Jun. 5, 2015, 1 page.

Reinhart et al., "Benchmarking of Commercially Available Cho Cell Culture Media for Antibody Production", Applied Microbiology and Biotechnology, vol. 99, No. 11, Apr. 7, 2015, pp. 4645-4657.

Schauer et al., "Probabilistic Density Maps to Study Global Endomembrane Organization", Nature Methods, vol. 7, No. 7, Jul. 2010, pp. 560-566.

Mdarsson et al., "IgG Subclasses and Allotypes: From Structure to Effector Functions", Frontier Immunology, vol. 5, Article 520, Oct. 20, 2014, 17 pages.

Australian Patent No. 2019450349, Notice of Acceptance for Patent Application, (2022).

International Application No. PCT/US2019/036379, International Search Report, (2019).

International Application No. PCT/US2019/036379, International Preliminary Report on Patentability (including amendment made under Chapter II PCT, (2021).

Al-Rubeai, "Antibody Expression and Production", Cell Engineering, vol. 7, p. 1-24, 2011.

Bandaranayake et al., "Recent Advances in Mammalian Protein Production", NIH Public Access, vol. 588, No. 2, Jan. 21, 2014, pp. 253-260.

Carroll et al., "The Selection of High-Producing Cell Lines Using Flow Cytometry and Cell Sorting", Expert Opinion on Biological Therapy, vol. 4, No. 11, 2004, pp. 1821-1829.

Huang et al., "An Efficient and Targeted Gene Integration System for High-Level Antibody Expression", Journal of Immunological Methods, vol. 322, 2007, pp. 28-39.

Jayapal et al., "Recombinant Protein Therapeutics from CHO Cells—20 Years and Counting", CHO Consortium, SBE Special Section, pp. 40-47, (2007).

Kim et al., "CHO Cells in Biotechnology for Production of Recombinant Proteins: Current State and Further Potential", Applied Microbiology Biotechnology, vol. 93, 2012, pp. 917-930.

Lai et al., "Advances in Mammalian Cell Line Development Technologies for Recombinant Protein Production", Pharmaceuticals, vol. 6, No. 5, ISSN 1424-8247, Apr. 26, 2013, pp. 579-603.

Lee et al., "Site-Specific Integration in CHO Cells Mediated by CRISPR/Cas9 and Homology-Directed DNA Repair Pathway", Scientific Reports, vol. 5, No. 8572, Feb. 25, 2015, pp. 1-11.

Meng et al., "Green Fluorescent Protein as a Second Selectable Marker for Selection of High Producing Clones From Transfected CHO Cells", Gene, vol. 242, Jan. 25, 2000, pp. 201-207.

Omasa et al., "Cell Engineering and Cultivation of Chinese Hamster Ovary (CHO) Cells", Current Pharmaceutical Biotechnology, vol. 11, 2010, pp. 233-240.

Ronda et al., "Accelerating Genome Editing in CHO Cells Using CRISPR Cas9 and CRISPy, a Web-Based Target Finding Tool", Biotechnology and Bioengineering, vol. 111, No. 8, Aug. 2014, pp. 1604-1616.

Sleiman et al., "Accelerated Cell Line Development Using Two-Color Fluorescence Activated Cell Sorting to Select Highly Expressing Antibody-Producing Clones", Biotechnology and bioengineering, vol. 99, No. 3, Feb. 15, 2008, pp. 578-587.

Wilkens et al., "Comparative Metabolic Analysis of CHO Cell Clones Obtained through Cell Engineering, for IgG Productivity, Growth and Cell Longevity", PLOS One, Mar. 13, 2015, pp. 1-15.

* cited by examiner

HYBRID YEAST CELL LINES FOR HIGH LEVEL PRODUCTION OF RECOMBINANT PROTEIN

REFERENCE TO RELATED APPLICATION

This application is a continuation of U.S. application Ser. No. 16/440,776, filed Jun. 13, 2019 (pending), which is a continuation-in-part of U.S. application Ser. No. 15/254,852, filed Sep. 1, 2016 and issued as U.S. Pat. No. 10,329,594 on Jun. 25, 2019, which claims the priority benefit of U.S. provisional application 62/213,880, filed Sep. 3, 2015. U.S. application Ser. No. 16/440,776, is also a continuation of international patent application PCT/US2019/036379, filed Jun. 10, 2019. The aforelisted priority applications are hereby incorporated herein by reference in their entireties for all purposes.

FIELD OF THE INVENTION

This application relates generally to the production of protein. It also relates to the modification and selection of cells and to transfection of such cells with a gene of interest to obtain cell lines for protein production at high productivity with improved biological and pharmacological characteristics.

BACKGROUND

Biological agents constitute a continually growing proportion of the market for pharmaceuticals. They have higher specificity than other agents, leading to more targeted efficacy with fewer side effects. With it comes a burgeoning need for improved means of industrial production, with greater productivity and lower cost.

Some therapeutic proteins have a therapeutic dose and dosing schedule that may require more than 10 grams of protein per patient per year. Current levels of protein production are generally no more than 4 g per liter of culture fluid, and are more typically less than 2 g per liter. To supply the market for a particular protein product, it may be necessary to produce 400,000 kg per year. This means that 100 million liters of culture medium would need to be processed—about the volume of 40 Olympic® sized swimming pools—which in turn would require several dedicated $1 billion manufacturing facilities.

Recent advances in mammalian protein production are discussed in A. D. Bandaranayake and S. C. Almo, FEBS Lett 2014, 588(2): 253-260; and T. Lai et al., Pharmaceuticals 2013, 6:579-603. Cell engineering and cultivation of Chinese Hamster Ovary (CHO) cells is reviewed in T. Omasa et al., Current Pharmaceutical. Biotechnology, 2010: 11, 233-240; C. A. Wilkens and Z. P. Gerdzen, PLOS ONE, Mar. 13, 2015; and J. Y. Kim et al., Appl. Microbiol. Biotechnol. 2012, 93:917-930. Multiplex genome engineering using systems such as CRISPR/Cas 9 is reviewed by L. Cong et al., Science 2013, 339(6121):819-823; Y. Huang et al., J. Immunol. Methods 2007, 322:28-39; J. S. Lee et al., Science Reports, Feb. 25, 2015; and P. Mali et al., Nat. Methods 2013, 10(10):957-963.

U.S. Pat. No. 5,607,845 (Spira et al., Pharmacia & Upjohn) proposed a method for obtaining an increased production of a producing cell line using a fusion protocol. U.S. Pat. No. 6,420,140 (Hori et al., Abgenix Inc.) proposed production of multimeric protein by a cell fusion method. Genome editing in CHO cells using CRISPR/Cas9 and CRISPy is reviewed by C. Ronda et al., Biotechnol. Bioeng. 2014, 111:1604-1616.

None of the technology described so far has the features and benefits of the technology of this invention, as described in the sections that follow.

SUMMARY OF THE INVENTION

Using previously available technology, production of therapeutic proteins (such as antibodies) has been expensive, requiring large volumes of culture medium and complex infrastructure. This disclosure provides substantially increased protein production yields on a per-cell basis, reducing the cost of commercial production and potentially improving product quality.

Model cell lines described in this disclosure are adapted for high levels of protein production. In principle, the invention can be implemented on any originating eukaryotic cell line, including but not limited to mammalian cells, insect cells, and yeast cells. The cells are screened for one or more characteristics that support protein production on a basis that is not necessarily specific for a particular protein: for example, the density of endoplasmic reticulum in the cell, the density of Golgi apparatus, and/or the level of other desired phenotypic features, compared with other cells in the starting mixture. The selected cells have increased capacity to produce protein or other gene product from a transgene. The selected cells may or may not show increased production from endogenous genes, since endogenous genes are subject to further regulatory constraints. A gene encoding a therapeutic protein is typically transfected into the cells before, after, or during one or more cycles of selection. Depending on the chosen protein, cell lines may be obtained that produce eight grams of protein per liter or more of culture fluid.

One aspect of this invention is a method of obtaining a cell line adapted for high-level production of protein-based pharmaceuticals. The originating cell population is typically heterogeneous in terms of protein production capacity, and/or it may be treated in a manner such that at least some of the cells contained therein have an ability to produce an increased amount of protein per cell than the cell population as a whole. For example, a mixture of cells is treated such that the mixture forms one or more cell hybrids, each comprising all or part of the genome of two or more cells from the mixture. Cells are selected from the population to obtain a producer cell population that is enriched for a higher density of one or more subcellular organelles that support increased production and/or secretion of protein, compared with other cells in the starting mixture. The originating mixture may consist essentially of cells from a single cell line, exemplified by Chinese Hamster Ovary (CHO) cells, or a combination of two or more different cell lines.

When this disclosure refers to a "producer cell line," what is meant is a cell line that is suitable for production of a gene product, such as for commercial use or sale. The technology put forth in this disclosure explains how to obtain a producer cell line with special properties that enable the cells to produce the gene product at a high level (per cell, or per culture volume) and/or with particular features of interest. A cell line that has been selected according to this technology may or may not contain a recombinant transgene for production of a particular product, since the transgene can be introduced before or after selection. Whether or not a transgene is present, a cell line created in accordance with this invention has the special properties that enable it to be a high level producer of product once the transgene has been introduced into the cell. Such special properties may include a relative enrichment for intracellular organelles involved in protein production, such as endoplasmic reticulum or Golgi apparatus. The capability of the cells for high level production from a transgene does not necessarily imply that the cells also have a capability for high level production from endogenous genes: in fact, if the increased production capability is selective for producing a target gene product encoded by the transgene, the purity of the target (compared with total cellular production) will also be increased, which may facilitate purification.

The method for selecting suitable high producer cells may include one or more of the following procedures in any combination:

- selecting individual cells or hybrids that have a relatively high density of endoplasmic reticulum per cell, compared with other cells in the mixture;
- selecting individual cells or hybrids that have a relatively high density of Golgi apparatus, compared with other cells in the mixture;
- incubating cells with a vital dye that stains endoplasmic reticulum and/or Golgi, and sorting cells according to the amount of the vital dye associated with each cell;
- expressing a fusion protein in cells in the mixture, wherein the fusion protein contains a peptide that generates an optical signal (such as GFP or luciferase) fused with a peptide that is processed by the endoplasmic reticulum and/or the Golgi apparatus, whereupon cells can be selected that express the optical signal at a higher level than other cells in the mixture.

The method for obtaining the high producer cells may further comprise one or more of the following procedures:

- selecting cells that grow faster, or that grow better under specified culture conditions;
- binding the cells with antibody specific for a cell surface ligand (the antibody optionally labeled or linked to a particle), and selecting cells labeled with the antibody, thereby obtaining a subpopulation that is enriched for cells that express the ligand;
- selecting cells that produce a relatively high level of a marker protein, compared with other cells in the mixture, wherein the marker protein is secreted from the cell and/or expressed on the cell surface, such as secreted alkaline phosphatase or secreted luciferase;
- selecting cells that produce a preferred glycosylation pattern or density on a marker protein, compared with other cells in the mixture; and
- culturing the producer cell population; and re-sorting cells therein for the same feature, thereby obtaining a subpopulation that is further enriched for cells in which an increased density of the subcellular organelles is stably inheritable.

A producer cell line for a particular target protein can be obtained according to this disclosure, for example, by transfecting cells from a cell line that has already been selected for high levels of protein production with a transgene gene encoding the target protein. Optionally, further selection for high levels of production can continue after transfection. Alternatively, a transgene encoding a protein of interest can be transfected into a starting cell population, following which cells are selected that produce a high level of protein product expressed from the gene of interest, compared with other cells in the mixture. In either case, the transgene may be inserted into the genome of the cells either by random insertion, or at a location that is pre-selected as permitting or supporting a high level of transcription, compared with other locations in the genome. A producer cell line for the target protein can then be established from the transfected and selected cells.

By way of example, the gene of interest may encode an antibody heavy chain, an antibody light chain, or a single-chain antibody. The producer cell line may express both an antibody heavy chain and an antibody light chain that combine to produce an antibody having a desired specificity. The producer cell line may express a therapeutic enzyme, a hormone, a growth factor, or a protein that is a naturally occurring component of blood.

Another aspect of the invention is a cell line produced according to the methods provided in this disclosure that has been selected for high levels of protein production—either before or after it has been genetically modified to express a target protein. Such a cell line may have features selected from the following: a genome that contains part or all of the genome of two or more parental cell lines, a higher concentration of endoplasmic reticulum and/or Golgi apparatus compared with any of the parental cell lines, and a capacity to produce a particular level of protein from one or a combination of recombinantly inserted genes, quantitated as described later in this disclosure. The producer cell line may or may not be clonal.

Aspects of the invention that are of current commercial interest to the inventor are indicated by the appended claims. Other aspects of the invention will be apparent from the description that follows.

DETAILED DESCRIPTION

Figure 1:
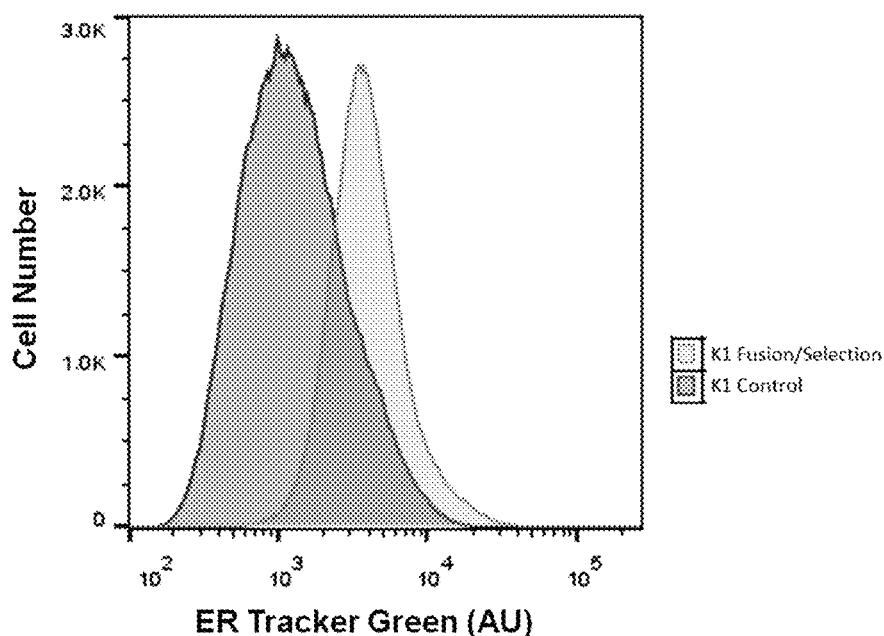
FIG. 1 shows the cell frequency profile for endoplasmic reticulum (ER) staining in native CHO cells, compared with CHO cell autotypic hybrids.

This disclosure provides improved cell lines for manufacture of protein-based pharmaceutical agents, considerably reducing the cost of commercial production. The cell lines are obtained by selecting cells from a mixed population for one or more characteristics that support protein production on a non-specific basis, such as the level of endoplasmic reticulum, Golgi apparatus, and/or other desired phenotypic features, compared with other cells in the starting mixture. Particularly effective producer cell lines can be obtained by preparing the cells for functional selection by making cell hybrids. A gene encoding a therapeutic protein of interest may be transfected into the cells before or after one or more cycles of fusion and selection.

Context

New biopharmaceutical products are coming on line at the rate of about 100 per year, while competition in the production of biosimilars continues to increase. There is a clear need for technology that can reduce the culture volume and cost required for production of these products.

This disclosure provides technology that allows product of protein biologicals at a productivity that surpasses current standards: potentially as much as 8 g per liter or more. The high efficiency producer cell lines described here can be used for industrial applicability in several ways. Regarding biosimilars, companies with brand-name products could maintain a marketing advantage by lowering their product cost structure. Similarly, companies producing biosimilars would compete with the brand-name products on cost. The cell lines provide considerable production flexibility by increasing capacity of existing plants; allowing production of more protein from fewer or smaller facilities; and reducing cost and time-to-clinic for new products.

Producer cell lines that generate high levels of a target protein are obtained by screening and sorting a mixed cell population for individual cells that are better equipped for greater or more rapid production of protein on a per-cell basis.

Making Cell Hybrids

Individual high producer cells can be selected from any cell population that is heterogeneous in this respect, as described in the section that follows. Many single cell lines (such as CHO cells) are sufficiently diverse at the outset in terms of gene content and intracellular apparatus in the proliferating cell population that they can be sorted and selected for high producer cells directly from a standard culture.

Optionally, to improve final product yield or enhance the sorting process, the user may prepare cells for sorting by taking one or a combination of techniques that will either enhance heterogeneity of levels of protein production within the cell population, or generally increase the levels of protein production for the cells population as a whole, or a subpopulation thereof. Suitable techniques are those that alter the genome of the cells, for example, to increase or shuffle genes that contribute to the intracellular machinery involved in protein production or processing. Altering or shuffling the genome in this manner may yield many genetic variants with one or more of a variety of different properties, including levels of protein production and growth rate.

The maker of this invention has discovered that cells suitable for protein production can attain a higher level of production by fusing with other cells. Without limiting practice of the invention, it is hypothesized that fusing two cells together is partly additive in terms of the components, genetics, or genetic control of the cells that participate in protein production. It is beneficial if the improved characteristics breed true. Accordingly, after cells are fused, they are typically subject to multiple rounds of culturing and selection for phenotypic characteristics of interest. The resulting cells may be aneuploid or otherwise retain all or part of the genomes of parental cells that encode cell components involved in protein production.

Model cells suitable for fusion are cell lines that have already been employed for industrial protein production, such as CHO cells, mouse myeloma NS0 cells, mouse myeloma SP2/0 cells, Human Embryonic Kidney (HEK) 293 cells, and Baby Hamster Kidney (BHK-21) cells. Also suitable are other Chinese Hamster cell types (for example, breast and liver cells that make secreted protein), human cell lines, and invertebrate cells, such as insect and mollusk cells that may have desired glycosylation properties. In the context of this disclosure, a "cell line" is a population of cells that can be propagated continually, extensively, or indefinitely in tissue culture. A starting cell line is typically heterogeneous in terms of one or more phenotypic features that relate to the amount of protein from a transgene that the cell will produce. When cultured, a producer cell line obtained according to this disclosure may produce progeny that are heterogeneous, substantially homogeneous, or clonal.

Cell fusion is performed by obtaining a cell mixture of cells to be fused: (a plurality of cells from one cell line, or more than one cell line, or a mixture of at least one cell line and at least one primary cell population. The cell mixture is then subjected to an appropriate fusion protocol: for example, by culturing under culture conditions that promote the formation of hybrids, by conducting an electrofusion, by combining with a fusogenic virus such as Sendai virus, by placing cells into contact (for example, by gentle centrifugation), by treating with a fusogenic agent such as polyethylene glycol (PEG), or using any effective combination thereof.

For purposes of this disclosure, cells that have been made by fusing two or more cells together may be referred to as autotypic hybrids (cells from the same cell line fused together), isotypic hybrids (cells having the same genotype), allotypic hybrids (cells from different individuals of the same species having different genotypes), and xenotypic hybrids (cells from different species). Autotypic hybrids are typically formed using a population of cells that consists essentially (that is, at least 99%) of cells from a single cell line. The other types of hybrids are typically formed using cell populations from two or more cell lines which have potentially complementary properties. The disclosure also includes the fusion of one or more cell populations isolated or obtained from primary sources with themselves or with established or cloned cell lines.

Cells may be fused into hybrids using any suitable technique. For example, cells may be cultured in the presence of a fusogenic agent and/or under culture conditions that promote the formation of hybrids, or may be forced into contact, for example, by gentle centrifugation, optionally in combination with a fusogenic agent such as polyethylene glycol (PEG). Typically a fused cell is obtained by fusing two cells together, although fusion of three or more cells is possible. It is recognized that fusion of two different cell populations will result in mixed cell products (isotopic, allotypic, or xenotypic hybrids, depending on the parental cell lines), and autotypic hybrids. Autotypic or isotopic hybrids can be separated from allotypic or xenotypic hybrids, if desired, using fluorescently labeled or surface bound antibody specific for a ligand expressed on one of the cell lines in the mixture, but not another.

All such combinations come within the scope of this invention, unless explicitly indicated otherwise. It may be beneficial to repeat the cell fusion within a population of hybrids to enhance the effect further, and/or cross-hybridize with other cell lines to imbue the ultimate cell line with additional beneficial characteristics. Thus, the fusion and selection steps may be done iteratively twice, three or four times, or more.

Selecting High Producer Cell Lines

A valuable insight of this disclosure is the idea that protein production can be increased by selecting cells from a mixed cell population for higher levels subcellular machinery or biochemistry that support increased protein production, compared with other hybrids or parental cells in the starting mixture. At least one of the phenotypic features is selected that is not necessarily specific for production of a particular protein. The feature is not simply the level of expression of a protein of interest or a surrogate. Rather, it is a feature that supports production of a wide range of different proteins. Such features include the relative density of subcellular organelles, particularly those involved in secretion of protein from the cell, and the relative level or concentration of enzymes that help finish or secrete a variety of different proteins.

Subcellular organelles involved in production of protein include the endoplasmic reticulum (ER) and the Golgi apparatus. Either or both of these can be measured and used as a basis for sorting or selection without damaging the cell using a vital dye, and the cells can be selected on the basis of the amount of dye that is associated.

Such dyes can be obtained commercially, for example from the company Molecular Probes. Examples of vital dyes for ER include:
  ER-Tracker™ Blue-White DPX (E12353)
  ER Tracker™ Green (glibenclamide BODIPY® FL) (E34251)
  ER-Tracker™ Red (glibenclamide BODIPY® TR) (34250)
  DiOC$_6$ (D273)
  DiOC$_5$ (D272).
Vital dies for Golgi apparatus include:
  NBD C6-6-ceramide (N1154)
  NBD C6-sphingomyelin
  BODIPY® FL C5-cerimide (D3521)
  BODIPY® TR ceramide (D7540)

Alternatively or in addition, the user can test expression-based labeling systems that would introduce a fluorescent protein targeted to ER or Golgi. They are fusion proteins comprising a portion that expresses an optical label, fused with a protein sequence that targets or is processed by the organelle to be labeled. Examples include the following:
Invitrogen:
  CellLight™ ER-GFP (C10590)
  CellLight™ ER-GFP (C10591)
  CellLight™ Golgi-GFP (C10592)
  CellLight™ Golgi-GFP (C10593)
Evrogen:
  pmKate2-ER (FP324)
  pFusionRed-ER (FP420)
  pTagRFP-Golgi (FP367)
  pTagRFP-Golgi (FP367)
  pFusionRed-Golgi (FP419)
Clontech:
  pDsRed2-ER Vector (632409)
  pDsRed-Monomer-Golgi Vector (632480)
  pAcGFP1-Golgi Vector (632464)

After staining with any of these dyes, cells may be selected (for example, by flow cytometry and sorting) that have on average a level of staining that is at least 1.2, 1.5, 2, or more than 2-fold higher than the parental cell line or lines, in terms of staining, for example, for ER, Golgi, or an optically labeled gene product.

Other features to select for may include but are not limited to phenotypic features, immunological features, and levels of protein production. Immunological features may include expression of a desired ligand by the cell (for example, secreted by the cell or expressed on the surface). Cells having an average level of expression of such markers that is at least 1.5, 2, 3, or 5-fold higher than the parental line can be selected, for example, by direct or indirect antibody labeling followed by FACS, or by binding to and releasing from antibody-coated microbeads. Immunological markers of interest include ligands that participate in production of secreted protein, such as glycosylation enzymes. Other sorting methods that can be used to screen cells according to this disclosure may include PCR-activated cell sorting, fluorescence in situ hybridization flow cytometry (FISH-PC), or FISH followed by laser capture.

Simultaneously or as a separate step, individual cells can also be selected from a mixed cell population for features that are desired for manufacturing purposes: such as cells that grow better under specified culture conditions, or that express relatively lower levels of one or more undesired contaminants.

To generate a cell line that is sufficiently stable to be used for manufacturing biological agents, the selected cells can be grown in culture through several cell divisions, and then re-tested to see if the desired feature is stable, for a total of two, three, or more than three times for each desired feature.

Transfecting Cells with a Gene of Interest

To generate a cell line expressing a protein of interest (a target protein), producer cells or their precursors can be transfected with a gene encoding the protein under control of a ubiquitous or mammalian promoter that causes expression in the host cell line. The level of production of the target protein can be determined in the course of processing using a transient transfection method to insert a protein expression cassette. Alternatively or subsequently, permanent transfection can be done that integrates the gene of interest or a marker gene into the genome of the cell line. Transfection can be done using liposome-based reagents (for example, Lipofectamine™ 2000 or FuGENE™ 6), calcium phosphate, electroporation, or infection with an adenovirus, retrovirus or lentivirus based vector.

Following transfection, the cells are tested for production or secretion of the target protein (typically after cloning or limiting dilution culture): for example, by enzyme-linked immunosorbent assay (ELISA). Cells or clones having increased production of the desired protein are selected. The objective can be an increase in protein production that is 1.5, 2, 4, 8, 12, 16, or 20-fold higher than the parental cell line; and/or production at a level of 6 g, 8 g, 10 g, 12 g, 15 g, or 20 g per liter of culture fluid under typical manufacturing conditions. The protein of interest can also be tested for other desired characteristics, such as the quality of sialylation or other aspects of glycosylation.

In principle, the transfection can be done either before, during, or after one or more cycles of fusion and selection for other features. For example, the fusion and selection can be done before transfection with the gene of interest, thereby establishing a parental cell line suitable for high-level production of a protein of the user's choice. Alternatively, the transfection can be done into the originating parental cell line, and used to track production levels during subsequent fusion and sorting steps, or to provide another basis for such sorting. Alternatively, the transfection can be done as an intermediate step, wherein the cells have already been subject to one or more cycles of fusion and selection for some other feature such as ER or Golgi, the resulting hybrid is transfected to express a protein of interest, and then subjected to further cycles of fusion and selection for expression of the protein of interest and/or other features referred to earlier in this disclosure.

The protein of interest can be the biological agent that is intended for manufacture: for example, an antibody heavy chain, an antibody light chain, a single-chain antibody, a therapeutic enzyme, a hormone, a growth factor, or a protein that is normally a blood component.

Another option is to develop a cell line using a marker protein as a proxy for the protein that ultimately will be manufactured: for example, secreted alkaline phosphatase or secreted luciferase. Again, the transfection can be done before, during, or after multiple cycles of fusion and selection, optionally using the level of expression of the marker as the selection criteria in one or more of the cycles. This creates a parental cell line that is optimized for expression of the marker protein, with the expectation that the beneficial characteristics of the cell line will be retained after further genetic alteration to produce a biological product of commercial interest.

Ultimately, once a cell line has been developed having a desired level of expression of the marker protein, the marker is then replaced with the protein of interest. Transfection can again be done randomly into the genome, using the techniques listed above, and expression of the marker protein is curtailed. Alternatively, the gene for the marker protein can be substituted with a gene that encodes the protein of interest using a targeted integration technique. Such techniques comprise, for example, CRISPR/Cas9, a zinc-finger recombinase (ZFR), or a transcription activator-like effector nuclease (TALEN). That way, the gene of interest is inserted into the genome of the cells from the producer cell line or the mixture at a location that is pre-selected as permitting or supporting a high level of transcription, compared with other locations in the genome.

For more information on the use of targeted integration techniques, the reader may refer to L. Cong et al., Science 2013, 339(6121):819-823; Y. Huang et al., J. Immunol. Methods 2007, 322:28-39; J. S. Lee et al., Science Reports, Feb. 25, 2015; and P. Mali et al., Nat. Methods 2013, 10(10):957-963; and C. Ronda et al., Biotechnol. Bioeng. 2014, 111:1604-1616.

Incorporation of Additional Features

The system and techniques provided in this disclosure can be combined with one or more alternative strategies to enhance cell growth or protein production for purposes of manufacture. Such techniques include vector and expression platform engineering, omics-based approaches, advances in gene delivery and integration, enhancement of protein production using chromatin opening elements, improvements in clone screening strategy, and so on.

Such techniques are discussed, for example, in A. D. Bandaranayake and S. C. Almo, FEBS Lett 2014, 588(2):253-260; T. Lai et al., Pharmaceuticals 2013, 6:579-603; T. Omasa et al., Current Pharmaceutical. Biotechnology, 2010: 11, 233-240; C. A. Wilkens and Z. P. Gerdzen, PLOS ONE, Mar. 13, 2015; J. Y. Kim et al., Appl. Microbiol. Biotechnol. 2012, 93:917-930; and C. Ronda et al., Biotechnol. Bioeng. 2014, 111:1604-1616.

One such feature suitable for incorporation is rapid proliferation. Mixed cell populations can be screened at any time during development of the producer cell line, either concurrently or as a separate step from the selection of cells that are equipped for high levels of protein production on a per-cell basis, based in content of endoplasmic reticulum and/or Golgi. Non-viable or slow-growing cells are removed or diluted out from the population during selection for faster growth.

By way of illustration, cells are cultivated in an appropriate culture medium and under appropriate conditions. A typical seed concentration of cells would be $2 \times 10^5$ cells/mL. The cells are cultivated for two days, then sub-cultivated by diluting cells to a concentration of $2 \times 10^5$ cells/mL. Repeat as desired, so that slower-growing cells are diluted-out. As the proportion of faster-growing cells in the mixed culture increases, the time between sub-cultivation steps can be decreased and/or the extent of cell dilution at each step can be increased.

Characteristics of Producer Cells

A cell line or mixed cell population that has been selected for high levels of protein production may be characterized in comparison with the parental or originating cell line by any one or more of several different parameters. For example, the selected cells may have: (1) a genome that is more aneuploid than the starting cells, containing part or all of the genome of two or more parental cell lines (which may or may not be the same), (2) a higher concentration of endoplasmic reticulum and/or Golgi apparatus compared with any one or all of the parental cell lines (for example, between 2 to 5-fold or 4 to 8 fold, or more than 2-, 4-, or 8-fold higher), (3) a capacity to produce a level of target protein per cell or per liter of culture fluid that is substantially higher than the parental cell line (for example, between 2 to 5-fold or 4 to 8 fold, or more than 2-, 4-, or 8-fold higher), (4) a capacity to produce a particular amount of target protein per cell (for example, more than 50, 65, 75, 100, 150, 200, 300, or 500 pg/cell/day, or from 50 to 200 or 75 to 300 pg/cell/day); or (5) a capacity to produce a certain amount of target protein per volume of culture fluid (for example, at least 5, 8, 12, 20, or 30 grams, or between 8 and 20 or between 10 and 50 grams of protein per liter of culture fluid.

For the purpose of making such comparisons, the producer cell line can be compared with a standardized population of the original cell line, either kept on hand, as part of the same system, or obtained from a reference source. For example, CHO derived producer cells may be compared with CRL-12023 cells from the American Type Culture Collection (ATCC®). This disclosure includes systems for high-level production of protein-based pharmaceuticals, comprising both a starting cell line, and a producer cell line derived therefrom that has a relatively high density of endoplasmic reticulum and/or Golgi apparatus per cell, as determined, for example, using one or more of the vital dyes listed above.

Benefits of this Technology

Depending on the mode of practice and application, aspects of the invention described in this disclosure can provide any of the following benefits in any combination:
- reduce the need to enlarge or build new GMP production facilities as market size increases;
- provide GMP production of kilogram quantities of finished protein product with relatively small or fewer bioreactors,
- reduce the cost of production of proven biological agents;
- create production cell lines suitable for high-level expression of a family of desired biological agents;
- decrease cloning or selection steps that are needed following integration of the gene to be expressed;
- improve product quality (for example, glycosylation); and
- provide high quality low volume research materials, reducing the time to clinical trials.

EXAMPLES

Example 1

The technology of the invention can be practiced using the K1 line of CHO cells (ATCC® CCL-61). A population of CHO cells grown in culture is fused so as to make isotypic hybrids according to the following protocol:
1. Centrifuge $10^7$ cells.
2. Discard supernatant
3. Break the pellet by gently tapping the bottom of the tube
4. Add 100 µL of 50% PEG over the period of one minute, while mixing the cells with a pipette tip
5. Continue stirring the cells for one additional minute
6. Add 100 µL of growth medium over one minute while mixing
7. Add 300 µL of growth over three minutes while mixing
8. Slowly add mL. of growth medium
9. Incubate at 37 degrees C. for five minutes
10. Centrifuge 11. Re-suspend the pellet in 20 mL of growth medium and transfer to a 125-mL culture flask
12. Culture normally.

Alternatively, an electrofusion procedure is employed using ECM2001 pulse generator (BTX). $10^7$ cells are centrifuged and resuspended in 1 mL of Cytofusion™ Medium C, then transferred into the fusion chamber. Cells are aligned with an alternating current pulse of 150 V/cm for 10 seconds. Cell fusion is triggered by a single square wave direct current pulse of 1200 V/cm for 25 μsec. Cells are allowed to rest for 5 min., centrifuged, then resuspended in growth medium and cultured normally.

Alternatively, a virus-induced fusion protocol may be employed. Various protocols exist using Sendai virus: for example, using a GenomONE™ HVJ-E Kit (Cosmo Bio USA): Cells are centrifuged and resuspended in ice cold cell fusion buffer at $2\times10^5$ cells/25 μL. 2.5 μL of an ice-cold HVJ-E (Sendai virus membranes) suspension is added to the cells and mixed by tapping. Mixture is incubated on ice for 5 min; then at 37 deg C. for 15 min. Growth medium is added to the mixture and it is transferred into a six-well plate for culture.

Labeling and sorting for subcellular organelles can be done as follows. The cells are centrifuged and washed once with HBSS buffer. A 1 μM solution of ER-tracker Green and/or ER-tracker Blue/White is prepared in HBSS. The cells are re-suspended in staining solution and incubated at 37 deg C. for 30 minutes. The cells are then washed with PBS.

If cells are to be used for analytical FACS, they are re-suspended in PBS; if they are to be sorted, they are re-suspended in PBS supplemented with 1% FBS. Ten percent of the viable population exhibiting the highest amount of staining with ER-Tracker dye was collected. The cells are collected into tubes containing growth medium, centrifuged, re-suspended in fresh medium, and then cultured normally.

Example 2

CHO-K1 cells were exposed to a PEG-assisted fusion procedure. The cells were allowed to recover for one week, then the procedure was repeated for a total of three times. Following recovery from the third fusion, the cells were stained with vital ER-tracking dye (ER-Tracker™ Green (glibenclamide BODIPY® FL); Invitrogen, E34251) and sorted using a FACSAriaII™ cell sorter (BD Biosciences). Ten percent of the viable population exhibiting the highest amount of staining with ER-Tracker dye was collected. Following a two-week recovery in culture, the cells were exposed to a final fusion, stained with ER-tracking dye, and analyzed using a LSRII™ flow cytometer (BD Biosciences).

To measure protein production in the fused cells, and the parental CHO population, the cells were transfected to express secreted alkaline phosphatase (SEAP). The transfection was performed as follows:
1. Centrifuge $10^6$ cells.
2. Discard supernatant
3. Resuspend in 100 μL Cell Line Nucleofector™ Solution T
4. Add 2 μg SEAP expression plasmid
5. Transfer to electroporation cuvette
6. Electroporate using Amaxa™ Nucleofector II and preset program U-023
7. Add 0.5 ml growth medium
8. Transfer cells into 6-well plate containing mL. growth medium per well FIG. 1 is the FACS (florescence-activated cell sorting) profile of the CHO cells after fusion and staining for levels of endoplasmic reticulum (ER). Fused cells showed a higher average level of ER compared with the starting CHO cell line.

Figure 2:
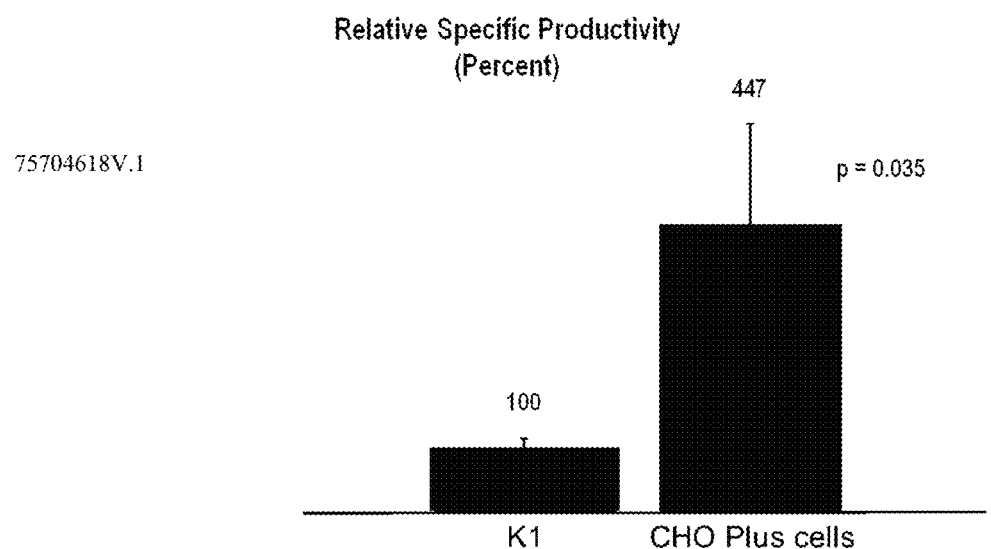
FIG. 2 shows the relative level of expression of alkaline phosphatase transfected into native CHO cells, compared with CHO cell autotypic hybrids. The expression in the fused cells shows over 4-fold improvement ($p<0.05$).

FIG. 2 shows the transfection results (specific productivity of secreted alkaline phosphatase). The expression of the marker protein in the fused cells is shows over 4-fold improvement.

For all purposes in the United States of America, each and every publication and patent document referred to in this disclosure is incorporated herein by reference in its entirety for all purposes to the same extent as if each such publication or document was specifically and individually indicated to be incorporated herein by reference.

While the invention has been described with reference to the specific embodiments, changes can be made and equivalents can be substituted to adapt the invention to a particular context or intended use as a matter of routine experimentation, thereby achieving benefits of the invention without departing from the scope of what is claimed.

The invention claimed is:

1. A method of obtaining a hybrid yeast cell line adapted for high-level production of protein, comprising:
   (a) fusing together and culturing individual cells in a starting population of yeast cells whereby a plurality of cell hybrids is formed, each comprising two or more of said individual cells; then
   (b) sorting the cell hybrids according to density of endoplasmic reticulum and/or Golgi apparatus per cell hybrid; and
   (c) selecting and recovering cell hybrids that have a relatively high density of endoplasmic reticulum and/or Golgi apparatus per cell hybrid compared with other cell hybrids sorted in step (b);
   thereby obtaining a yeast cell line that supports increased production and/or secretion of protein compared with parental cells in the starting population.

2. The method of claim 1, wherein the starting population cultured in step (a) consists essentially of cells from a single yeast cell line.

3. The method of claim 1, wherein the starting population cultured in step (a) comprises two or more different yeast cell lines.

4. The method of claim 1, wherein step (c) includes selecting and recovering cell hybrids that have a relatively high density of endoplasmic reticulum per cell, compared with other cell hybrids or parental cells in the starting population.

5. The method of claim 1, wherein step (c) includes selecting and recovering cell hybrids that have a relatively high density of Golgi apparatus, compared with other cell hybrids formed in step (a) or parental cells in the starting population.

6. The method of claim 1, wherein step (b) includes incubating cell hybrids with a vital dye that stains endoplasmic reticulum and/or Golgi, and sorting cell hybrids according to the amount of the vital dye associated with each cell hybrid.

7. The method of claim 1, comprising selecting cell hybrids that produce a relatively high level of a marker protein, compared with other cell hybrids formed in step (a), wherein the marker protein is secreted from or expressed on the surface of each of the selected cell hybrids.

8. The method of claim 1, further comprising culturing cell hybrids obtained following step (c) and resorting the cell hybrids according to the density of endoplasmic reticulum and/or Golgi apparatus, thereby obtaining a subpopulation that is enriched for cell hybrids in which an increased density of endoplasmic reticulum and/or Golgi apparatus is stably inheritable.

9. The method of claim 1, further comprising transfecting the cell hybrids with a gene of interest to obtain a transfected cell population, and selecting transfected cells from the transfected cell population that produce higher levels of a protein product of the gene of interest, relative to other cells in the transfected cell population, wherein the transfecting is performed on cells formed in step (a) or selected and recovered in step (c).

10. A yeast cell line that comprises a transgene that encodes a target protein, wherein the yeast cell line has been prepared by the following process:
    (a) fusing together individual cells in a starting population of yeast cells whereby a plurality of cell hybrids is formed, each comprising two or more of said individual cells; then
    (b) sorting the cell hybrids formed in step (a) according to the density of endoplasmic reticulum and/or Golgi apparatus per cell hybrid;
    (c) selecting and recovering cell hybrids sorted in step (b) that have a relatively high density of endoplasmic reticulum and/or Golgi apparatus per cell; and
    (d) establishing said yeast cell line from the cell hybrids selected and recovered in step (c).

* * * * *